United States Patent
Chaney

[19]

[11] Patent Number: 5,855,547
[45] Date of Patent: Jan. 5, 1999

[54] BULB PUMP FOR IMPOTENCE THERAPY AND OTHER PURPOSES

[76] Inventor: John L. Chaney, 156 Broad St., Box 790, Lake Geneva, Wis. 53147

[21] Appl. No.: 682,120

[22] Filed: Jul. 17, 1996

[51] Int. Cl.$^6$ ........................................................ A61F 5/00
[52] U.S. Cl. ................................................................. 600/38
[58] Field of Search ................................. 600/38, 41, 498, 600/499; 128/686, 680–83, 677

[56] References Cited

U.S. PATENT DOCUMENTS

| | | | |
|---|---|---|---|
| 4,407,275 | 10/1983 | Schroeder | 600/38 |
| 4,968,294 | 11/1990 | Salama | 600/30 |
| 5,244,453 | 9/1993 | Osbon et al. | 600/38 |

FOREIGN PATENT DOCUMENTS

| | | | |
|---|---|---|---|
| 1497441 | 1/1978 | United Kingdom | 600/38 |

*Primary Examiner*—John P. Lacyk
*Attorney, Agent, or Firm*—Ryan, Maki, Mann & Hohenfeldt

[57] ABSTRACT

A vacuum pump has a bulb whose wall is composed of elastic material and has a first protuberance projecting into the interior of the bulb and a second protuberance projecting outwardly of the bulb. The first protuberance has an air intake passageway for communicating with a chamber that is to be evacuated and the second protuberance has an air exhaust passageway communicating with the interior of the bulb. Each of the protuberances has a slit that is pressed closed by the inherent elasticity of the protuberance material so they serve as check valves. When the bulb is squeezed air pressure developed in the bulb acts on the interior air intake protuberance to close its slit and the slit in the exterior air exhaust protuberance is forced open to exhaust air from the bulb. When the squeezed bulb is relieved the elastic bulb expands to create negative pressure in the bulb which closes the exhaust slit and opens the air intake slit.

10 Claims, 2 Drawing Sheets

U.S. Patent  Jan. 5, 1999  Sheet 1 of 2  5,855,547
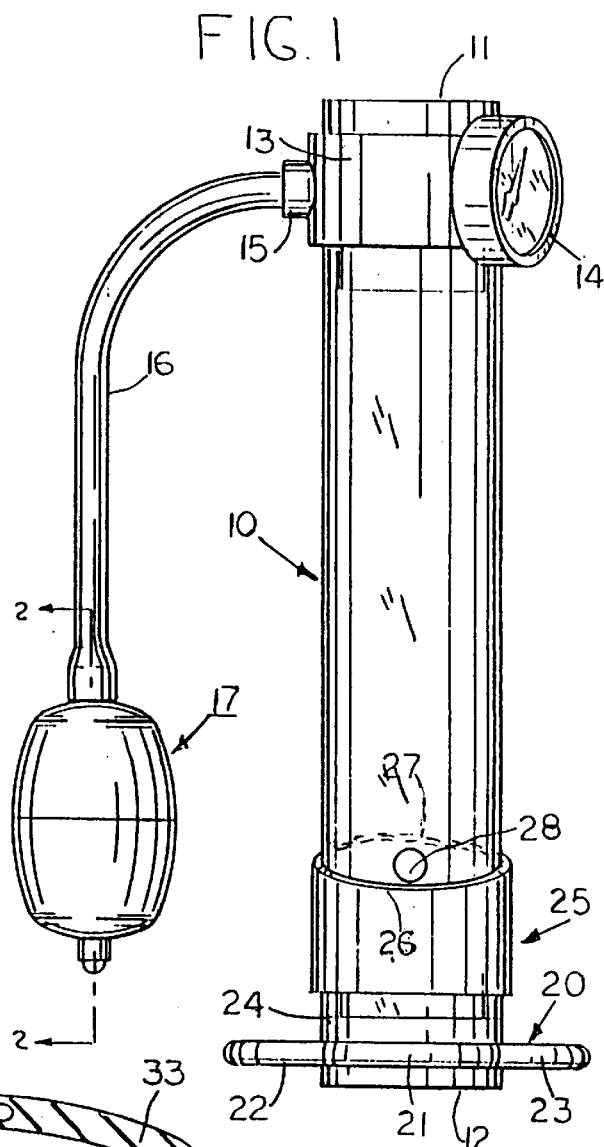
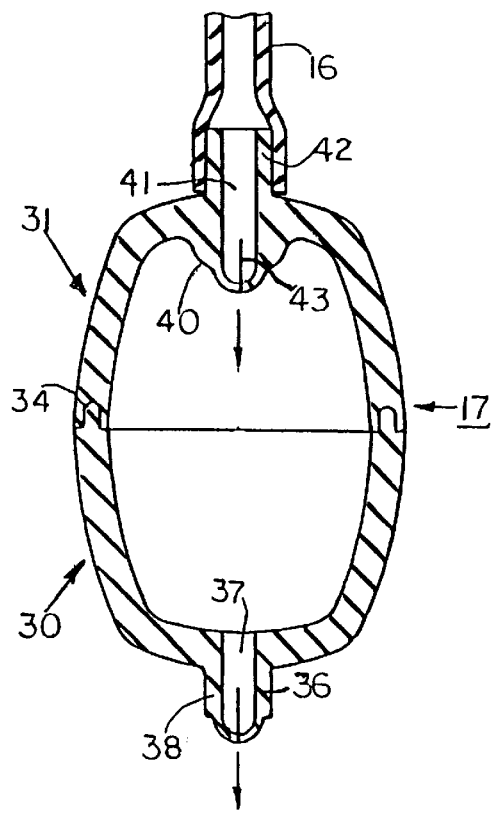
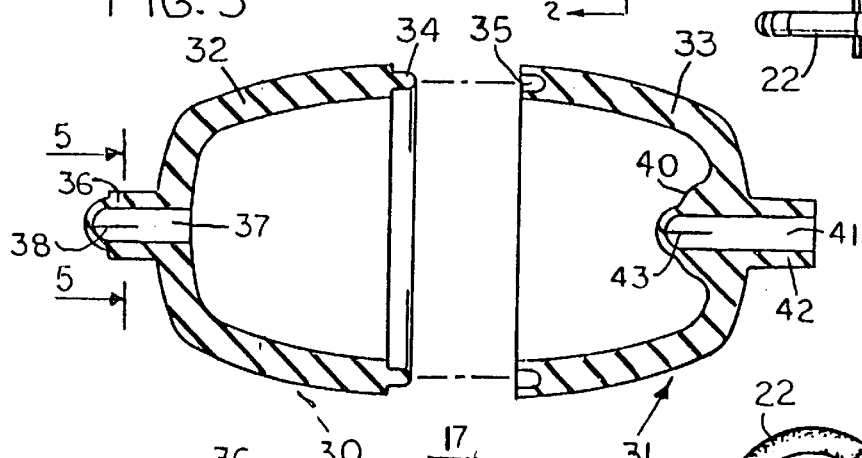
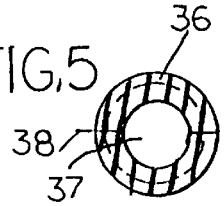
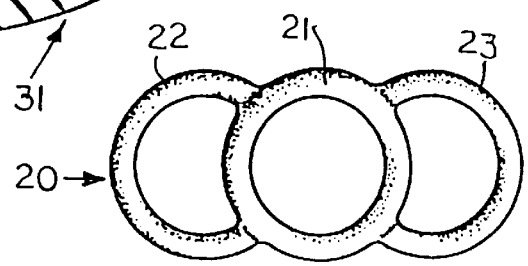

BULB PUMP FOR IMPOTENCE THERAPY AND OTHER PURPOSES

BACKGROUND OF THE INVENTION

The invention disclosed herein pertains to a manually operated bulb pump that has a variety of uses, but will be described in connection with creating a partial vacuum in a cylinder into which a male penis extends for inducing blood into the penis to thereby cause an erection.

Vacuum therapy is a widely used procedure for treating impotence. The procedure requires a man to dispose his penis in the open end of an otherwise closed tube or cylinder to which a vacuum pump is connected. The open end of the cylinder is pressed against the body circumjacent the penis base to effect a seal. Then the vacuum pump is operated to make the pressure in the cylinder negative relative to the atmosphere and relative to the body's blood pressure. As a result, the blood pressure in the body, being relatively higher than the pressure in the cylinder, causes the penis to become gorged with blood under pressure and expanded which is what occurs incidental to obtaining of a natural erection. When the erection is achieved, an elastic ring is slipped off the cylinder and onto the base of the penis to prevent backflow of venous blood and thereby maintain pressure in the penis and the erection.

The vacuum therapy procedure and existing equipment for practicing vacuum treatment are described and shown in U.S. Pat. No. 5,195,943 which is owned by the applicant of this application.

Pumps presently used for evacuating penile cylinders represent a substantial percentage of the production costs of the therapy system. A preexisting type of vacuum pump is shown in the patent cited above. The pump has a cylindrical body mounted coaxially to the penile cylinder to close the end opposite from the end of the cylinder into which the penis is inserted. A piston is manually recriprocable in the pump cylinder with an external handle and is coaxial with the pump and cylinder. A check valve is required in the pump to facilitate exhausting air from the cylinder and to prevent atmospheric air from leaking into the cylinder. The pump requires molding of several plastic parts and requires assembling of parts including a check valve which is labor intensive and expensive.

Besides high manufacturing cost and the use of movable parts, another disadvantage of this type of pump is that the user must reach out and away from the body with one hand to grasp the piston operating handle of the pump while holding the vacuum cylinder against the body tightly enough to avoid breaking the body seal too.

Another type of hand operated plastic vacuum pump that is widely used in connection with penile vacuum therapy is one that has been used for decades in chemical laboratories, for example, to create suction for accelerating filtering. This pump has a cylinder mounted to a pistol grip handle and a piston rod connected to a trigger lever that is squeezed repeatedly to reciprocate a piston until a pressure gauge on the vacuum cylinder registers a negative pressure of about 10 to 12 inches of mercury. This is the customary pressure or vacuum that is generally recommended for the treatment. The several separately molded parts of the pump plus the check valves and assembly time results in a rather costly pump. This type of pump is usually connected to the penile cylinder with flexible tubing.

SUMMARY OF THE INVENTION

The new bulb pump design disclosed herein is distinguished over prior pumps by its simplicity, durability, lack of moving parts, inherent check valves, ease of use and low manufacturing cost.

The new pump is comprised of a hand held bulb composed of an elastomeric material. The bulb can be connected to any chamber in which a partial vacuum or negative pressure relative to atmospheric pressure or blood pressure is desired to be created. The bulb has a protuberance, comprising an intake check valve, projecting from one end of the bulb body into the interior of the bulb and has another protuberance, comprising an exhaust valve, at the opposite end projecting exteriorly of the bulb. The check valves are the epitome of simplicity in that they are created simply by making a razor slit in each of the protuberances. The protuberance that projects into the bulb has a tubulation exteriorly of the bulb that provides for attaching a hose for connecting it to a chamber, such as a penile vacuum cylinder, that is to be evacuated. The interiorly projecting protuberance acts as the air intake or suction check valve. The protuberance that projects outwardly of the bulb acts as the exhaust or discharge check valve which allows for discharge of air from the bulb into the atmosphere when the bulb is squeezed.

The method of making the bulb pump involves molding two nominally hemispherically shaped parts composed of an elastomeric material. One of the parts has the exteriorly projecting protuberance molded integrally with it. The other of the nominally hemispherically shaped parts has the interiorly projecting protuberance molded integrally with it. The two hemispheres, which are actually oblong, are joined together with adhesive to effect a seal between the two molded parts and thereby yield an oblong bulb.

To develop a vacuum in a chamber into which the flaccid penis is inserted, the bulb is taken in hand and squeezed to discharge air from it and then relieved to draw air into it from the chamber or cylinder. When the wall of the bulb is squeezed or collapsed, air is expelled from the bulb through the exhaust check valve constituted by the slitted protuberance that projects outwardly of the bulb.

During squeezing of the bulb the suction or air intake check valve constituted by the protuberance that projects inwardly of the bulb seals closed due to air pressure developed in the bulb by squeezing it. When the force of the hand on the bulb is relieved, the inherent resiliency of the elastomeric bulb causes it to restore to its normal inflated state in which case it draws air from the vacuum cylinder through the check valve constituted by the slit in the interiorly projecting protuberance. The bulb squeezing and relieving process is repeated until the gage on the penile cylinder indicates the desired negative pressure equivalent which is generally the pressure or partial vacuum that results in achieving an erection.

The vacuum level rating, that is, the maximum vacuum obtainable with the bulb pump is controlled in several ways for the sake of safety. First of all, it can be controlled by using an elastomeric material that has a particular durometer or stiffness. It can also be controlled by varying the wall thickness. The wall thickness and durometer of the elastomeric material can both be selected to produce a pump that has specific pumping speed and vacuum level limits.

In one embodiment of the bulb pump, the protuberances are slitted longitudinally to create intake and exhaust check valves and in another embodiment the protuberances are slitted transversely to create the intake and exhaust check valves.

How the foregoing features of the new pump are implemented will appear in the ensuing more detailed description of preferred embodiments which will now be set forth in reference to the accompanying drawing.

DESCRIPTION OF THE DRAWING

FIG. 1 is a side elevational view of an illustrative vacuum type erection obtaining apparatus equipped with the new bulb pump;

FIG. 2 is a longitudinal sectional view of the new pump completely assembled and ready for use;

FIG. 3 shows the two nominally hemispherical parts of the pump after they are molded, slitted to develop their check valves and are ready to be joined together;

FIG. 4 is a plan view of an elastic restrictor ring;

FIG. 5 is a transverse section taken on a line corresponding with 4—4 in FIG. 3;

DESCRIPTION OF A PREFERRED EMBODIMENT

Figure 6:
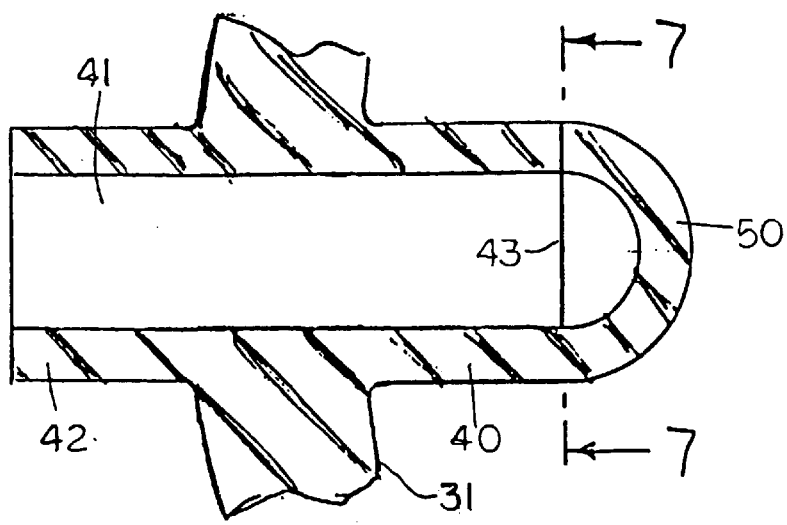
FIG. 6 is a sectional view of an alternative form of an intake check valve which is used in the bulb pump.

FIG. 1 shows a vacuum therapy system in which the new bulb type pump is used. The system comprises a cylinder 10 which is usually composed of a clear transparent plastic such as an acrylic material. The end of the cylinder marked 11 is closed. The opposite end 12 of the cylinder is open to provide for a male inserting his penis into the cylinder while the rim of the opening is pressed against the body surrounding the base of the penis. This procedure is demonstrated in previously cited U.S. Pat. No. 5,195,943. The upper end region of vacuum cylinder 10 is provided with an integrally molded collar 13 in which there is a not visible threaded hole which is provided for connecting a vacuum gage 14 to the cylinder. Collar 13 has a tubulation 15 for connecting the vacuum cylinder 10 with a flexible tube or hose 16 to the new bulb pump which is designated generally by the numeral 17. After a flaccid penis is inserted into cylinder 10 through the open end 12 and the open end is pressed sealingly against the body circumjacent the base of the penis, bulb pump 17 is operated to create a partial vacuum or negative pressure in cylinder 10. After a surprisingly small number of pumping cycles, consisting of alternate squeezing and relieving of the bulb, are executed sufficient vacuum is developed in cylinder 10 for arterial blood to fill the cavernous spaces in the penis to thereby cause it to become rigid and erect.

As is well known, it is necessary to apply an elastic restrictor ring to the penis before it is withdrawn from the vacuum cylinder 10 to prevent blood in the penis from flowing back into the venous system if loss of the erection is to be avoided. An elastic restrictor device is identified by the numeral 20 in FIGS. 1 and 4. The restrictor device is used for preventing outflow of pressurized blood from the penis. A suitable restrictor device 20 is shown in plan view in FIG. 4 and in profile in FIG. 1. The illustrative restrictor device is described in detail in U.S. Pat. No. 4,539,980 which issued to the applicant in this application. The device comprises a central elastic ring 21 which is usually round in cross section. Molded integrally with the central ring are two diametrically opposite elastic handles or gripping elements 22 and 23. Central ring 21 is stretched manually to fit it onto the end region 24 of vacuum cylinder 10 before the penis is inserted in the open cylinder end 12. After the erection is obtained, ring 21 is slid off region 24 to encircle the base of the penis. At this time the ring 21, being elastic, contracts and tightens on the penis base to prevent exiting of the pressurized blood from the penis on which maintenance of the erection depends. The ring device 20 can be slid off the vacuum cylinder end region 24 if desired using handles 22 and 23. However, it is preferred to push the ring device 20 off the cylinder by using the collar 25 which is rotatable on cylinder 10. The collar 25 is designed to act as a cam. It has an inboard end cut at an angle relative to its axis. Thus, it has a front edge 26 that is lower than its back edge 25. The front edge 26 is presently abutting a riser or boss 28 that is molded integrally with the wall of vacuum cylinder 10. When the user is ready to push the ring 20 off cylinder 10, the user rotates collar 25 in which case the back edge 27 of the collar slides along riser 28 which forces ring device 20 axially to cause transfer of the ring from cylinder 10 and to the base of the penis. The ring expelling device using a cam collar 25 is described in previously mentioned U.S. Pat. No. 5,195,943.

The parts of the new pump will now be described in detail. Attention is invited to FIG. 3. This figure shows that the pump is comprised of two major bodies 30 and 31 which are combined to produce a single closed bulb as is exhibited in FIG. 2. The bodies 30 and 31 may be characterized as cup-shaped, bell-shaped, dome-shaped, concavities, hemispheres, or hemispherical. The words hemisphere and hemispherical are arbitrarily selected as generic terms encompassing the named shapes and others. The bodies 31 and 32 are molded of a suitable elastomer such as natural rubber, silicone rubber, urethane, or the like which restores to its original shape after it is deflected, compressed, or distorted by a manual force and then released. Hemispheres 30 and 31 have rather thick walls 32 and 33 which, therefore, develop a self-restoring force which is strong enough for the assembled pump shown in FIG. 2 to generate a vacuum in penile vacuum cylinder 10 represented by at least 10 inches of mercury and up to a limit of 15 inches of mercury where the pump model is supplied for use in the vacuum impotence procedure. The self restoring force of the collapsed bulb can also be controlled in accordance with the durometer of the material out of which hemispheres 30 and 31 are made as indicated earlier.

FIG. 3 shows that the rim of hemisphere 30 has an annular axially extending tongue 34 and the rim of hemisphere 31 has an annular complementarily shaped groove 35. Adhesive is applied at the interface of the tongue and groove and the tongue 34 is then pressed into groove 25 to form the unitary bulb pump 17, depicted in FIGS. 1 and 2.

FIG. 3 shows that hemisphere 30 has an outwardly projecting integrally molded protuberance 36 comprising an exhaust or discharge check valve. The protuberance is optionally circular in cross section as shown in FIG. 5 and it has a bore or passageway 37 that is formed during molding of the elastomeric hemisphere 30. Before or after hemispheres 30 and 31 are sealed together an axially extending diametrical slit 38 is made in protuberance 36 with a razor sharp instrument, not shown. The inherent resiliency of the material of which the protuberance 36 is made keeps a releasable sealing pressure on the slit. The slitted protuberance 36 serves as an air exhaust check valve for the bulb pump, in accordance with the invention, whose function will be elaborated shortly hereinafter. This check valve allows air to exhaust from the bulb when the bulb is squeezed and prohibits inflow of air to the bulb when the hand squeezing pressure on the bulb is relieved.

As is also shown in FIG. 3, mating hemisphere 31 has an axially and inwardly projecting protuberance 40 comprising an intake check valve that is formed during molding of hemisphere 31. Protuberance 40 is generally circular in cross section and has an axially extending bore or passageway 41 which extends through a tubulation 42 that is provided for connecting the flexible tube 16 to hemisphere 31. Protuberance 40 has an axially extending slit 43 that is made with a razor sharp instrument before hemispheres 30 and 31 are sealed together. Slitted protuberance 40, according to the invention, serves as an air intake check valve that closes when the interior of the bulb become pressurized by squeezing it and opens when the squeezing force is released because of the negative pressure that exists in the expanding bulb after it is released.

A full operating cycle of the bulb pump will now be described in reference to FIG. 2. Assume that the bulb is connected by means of flexible tube 16 to the penile vacuum chamber 10. The bulb, as depicted, is presently in a quiescent state, that is, it is fully expanded. Slits 38 and 43 are closed by the inherent resiliency in their associated protuberances 36 and 40, respectively. Assume now that the bulb pump 17 is squeezed by the hand of a user. Squeezing the bulb causes a pressure increase in the interior which results in the air which was occupying the bulb to be discharged through exhaust check valve 36 whose slit opened because the air pressure built up in the bulb by squeezing it is greater than the force applied to the slit by the inherent elasticity of the protuberance and the pressure of the atmosphere. Meanwhile, with the bulb having been squeezed, the high pressure developed in the bulb is applied to protuberance 40 which, in conjunction with the force applied by the inherent resiliency of the protuberance, results in slit 43 being pressed closed. When the bulb is released from being squeezed its inherent resiliency tends to restore it to its quiescent state which means that the bulb expands. Expansion is concomitant with existence of a negative pressure in bulb 17 so that atmospheric pressure and the resiliency of external protuberance 36 causes slit 38 of the exhaust check valve to be pressed together or closed. On the other hand, the negative pressure in the bulb relieves the pressure acting on protuberance 40 of the intake check valve and allows air to be drawn through slit 43. This air is derived from therapy cylinder 10 which thereby experiences loss of air or development of a negative pressure relative to the atmosphere. Repeatedly squeezing and releasing the bulb as just described will after, after a few such cycles, reduce the pressure or increase the vacuum in cylinder 10 so that blood will flow into a penis extending through opening 12 and an erection is likely to be obtained.

Figure 7:
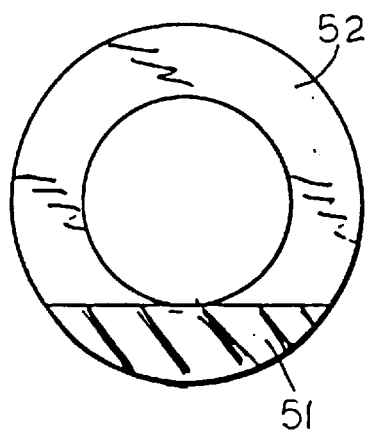
FIG. 7 is a transverse section taken on the line corresponding to 7—7 in FIG. 6; and, FIG. 8 is a sectional view of an alternative form of exhaust check valve which is used in the bulb pump.
Figure 8:
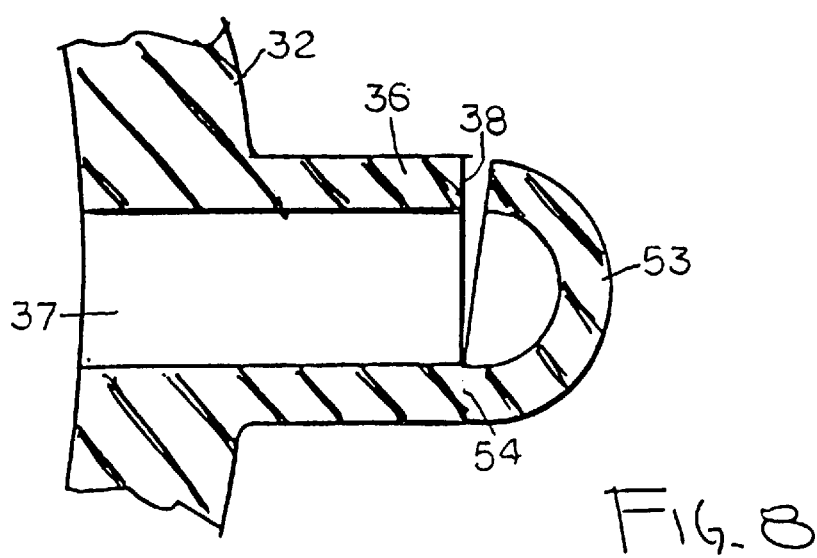

FIG. 6 shows in section a modified version of the intake check valve and FIG. 8 shows in section a modified version of the exhaust or discharge check valve. Insofar as is possible the parts of the valves in FIGS. 6,7 and 8 will be given the same reference numerals as are given to their counterparts in the FIG. 2 embodiment, for example.

Thus, the intake valve protuberance 40 projects inwardly of the bulb from the hemispherical bulb wall 31. The wall has a tubulation 42 onto which a flexible tube 16 can be attached for connecting the bulb to a chamber that is to be evacuated. The tabulation 42 and the protuberance 40 contain a passageway 41 for conducting intake air from a chamber that is being evacuated into the bulb. The main difference between the FIG. 6 and FIG. 2 intake valves is that in FIG. 6 the slit 43 is made part of the way across the protuberance 40 instead of longitudinally as in the previously described version. A valve cap or flap 50 remains attached to the protuberance 40 after the slit is made. The area of attachment 51 which is cross hatched in FIG. 7 serves as a hinge on which sealing flap 50 can yield to open the intake check valve when the flap has suction applied to it as is the case when the bulb is relieved after it has been squeezed during a pumping cycle. The flap or cap 50 seals against surface 52 under the force resulting from the inherent resiliency of the elastomeric hinge area 51.

The exhaust check valve shown in FIG. 8 results from making a transverse slit 38 in exteriorly projecting protuberance 36. The exhaust valve is shown in its open state as it would be when the bulb is being squeezed to exhaust a quantity of air that has been drawn from a chamber being evacuated. The exhaust check valve is urged to a closed condition by the inherent resiliency of the uncut area 54 that remains after protuberance 36 is partly slit through.

I claim:

1. A manually operable pump comprised of:

a bulb having a wall composed of elastic material, a first protuberance composed of said elastic material projecting from said wall inwardly of the bulb and having an air intake passageway, said protuberance having an air intake slit for communicating the interior of the bulb with said air intake passageway, a second protuberance composed of said elastic material and having an air exhaust passageway, said second protuberance having an air exhaust slit for communicating the interior of the bulb with said air exhaust passageway, squeezing said bulb to deform it causing air pressure to increase in said bulb for forcing said air exhaust slit to open and said air intake slit to close, and relieving said bulb after deforming it restoring said bulb to undeformed condition to create vacuum in said bulb that results in said air exhaust slit closing and said air intake slit opening for drawing air into said bulb.

2. A pump according to claim 1 wherein said slit in said first protuberance extends longitudinally of said first protuberance.

3. A pump according to claim 1 wherein said slit in said second protuberance extends longitudinally of said second protuberance.

4. A pump according to claim 1 wherein said slit in said first protuberance extends transversely partially through said first protuberance.

5. A pump according to claim 1 wherein said slit in said second protuberance extends transversely partially through said second protuberance.

6. A pump according to claim 1 wherein the thickness of said wall of the bulb and the durometer of said elastic material are varied to predetermine the level of vacuum that is developed by the pump.

7. A pump according to claim 1 wherein said inwardly projecting and outwardly projecting protuberances and their said passageways are coaxial.

8. A pump according to claim 1 including a tubulation extending integrally from said pump with the opening of the tubulation in communication with said air intake passageway.

9. A pump according to claim 1 wherein said bulb is composed of two nominally hemispherically shaped bodies each of which has an annular rim, one of the rims configured as an annular tongue and the other of the rims configured as a complementarily shaped annular groove, and the annular tongue is registered sealingly in said annular groove for said hemispherically shaped bodies to form said bulb.

10. A manually operated pump in combination with apparatus for aiding a male to obtain an erection, said apparatus comprising a chamber in which there is an opening having a rim for being pressed in releasable and sealable fashion against the body circumjacent the base of the penis while the penis is disposed in the chamber, said pump comprising a bulb having a wall composed of elastic material, a first protuberance composed of said elastic material projecting from said wall inwardly of the bulb and having an air intake passageway, said protuberance having an air intake slit for communicating the interior of the bulb with said air intake passageway, a second protuberance composed of said elastic material and having an air exhaust passageway, said second protuberance having an air exhaust slit for communicating the interior of the bulb with said exhaust passageway, squeezing said bulb to deform it causing air pressure to increase in said bulb for forcing said air exhaust slit to open and said air intake slit to close, and relieving said bulb after deforming it restoring said bulb to undeformed condition to create vacuum in said bulb that results in said air exhaust slit closing and said air intake slit opening for drawing air into said bulb, a connector on said chamber for connecting one end of a flexible tube to said chamber and a connector on said bulb for connecting the opposite end of said tube to said bulb in communication with said air intake passageway, such that said chamber becomes evacuated in response to alternatingly squeezing and relieving said bulb.

\* \* \* \* \*